United States Patent

Weber et al.

[11] Patent Number: 5,906,602
[45] Date of Patent: May 25, 1999

[54] SHAPED ABSORBENT CORES COMPRISING MULTIPLE PIECES OF ABSORBENT MATERIAL AND METHOD FOR MAKING SAME

[75] Inventors: Gerald Martin Weber, Loveland; Gerald Alfred Young, Cincinnati; Gregory Wade Taylor, Forest Park; Gary Dean La Von, Middletown, all of Ohio

[73] Assignee: The Procter & Gamble Company, Cincinnati, Ohio

[21] Appl. No.: 08/833,015

[22] Filed: Mar. 27, 1997

[51] Int. Cl.$^6$ ........................................ A61F 13/15
[52] U.S. Cl. ........................................ 604/385.1; 604/378
[58] Field of Search ................................ 604/385.1, 378

[56] References Cited

U.S. PATENT DOCUMENTS

| | | |
|---|---|---|
| 2,897,818 | 8/1959 | Perry, Jr. et al. . |
| 3,072,123 | 1/1963 | Davis . |
| 3,306,293 | 2/1967 | Marder et al. . |
| 3,563,242 | 2/1971 | Hedstrom et al. . |
| 3,875,837 | 4/1975 | Dussaud ........................... 83/46 |
| 4,331,501 | 5/1982 | Teed ................................ 156/383 |
| 4,336,803 | 6/1982 | Repke . |
| 4,413,996 | 11/1983 | Taylor ............................. 604/382 |
| 4,531,945 | 7/1985 | Allison ............................ 604/378 |
| 4,597,759 | 7/1986 | Johnson ........................... 604/385.1 |
| 4,643,726 | 2/1987 | Gegelys .......................... 604/368 |
| 4,670,011 | 6/1987 | Mesek ............................. 604/378 |
| 4,690,719 | 9/1987 | Lucas et al. .................... 156/201 |

(List continued on next page.)

FOREIGN PATENT DOCUMENTS 2 165 757  4/1986  United Kingdom .

Primary Examiner—Mickey Yu
Assistant Examiner—Bruce E. Snow
Attorney, Agent, or Firm—Roddy M. Bullock; W. Scott Andes; Jacobus C. Rasser

[57] ABSTRACT

Disclosed is a shaped absorbent core suitable for absorbing and retaining aqueous body fluids. The absorbent cores comprise a front panel and a back panel. The front and back panels are made from fluid absorbent material, and each has an inner end, an outer end, and two sides. The inner and outer ends of each front and back panel have a length, with the inner end of each being shorter than the outer length of each. The front and back panels may comprise multiple layers of absorbent material. The absorbent cores also comprise a center section made from fluid absorbent material having first and second ends. The first end of the center section is in fluid communication with the front panel by overlapping the front panel intermediate the front inner and outer ends, and the second end is in fluid communication with the back panel by overlapping the back panel intermediate the back inner and outer ends. A method of preparing a shaped absorbent core comprises the steps of providing at least one continuous rectilinear web of first absorbent material having a longitudinal axis and a pair of lateral edges defining a first width. A continuous rectilinear web of second absorbent material having a longitudinal axis and a pair of lateral edges defining a second width wider than the first width of the first absorbent material is formed with opposing generally arcuate notched areas in the lateral edges at spaced intervals along the web of second absorbent material. The web of second absorbent material is severed transversely along a line intersecting the opposed generally arcuate notched areas at spaced intervals to form sections having opposed notched ends The sections are then positioned such that the notched ends are spaced apart and overlap the continuous rectilinear web of first absorbent material, forming layers of absorbent material. Then the layers of absorbent material are severed transversely at a point intermediate the notched ends.

15 Claims, 10 Drawing Sheets

U.S. PATENT DOCUMENTS

| | | | |
|---|---|---|---|
| 4,738,675 | 4/1988 | Buckley et al. | 604/380 |
| 4,795,453 | 1/1989 | Wolfe | 604/385.1 |
| 4,842,594 | 6/1989 | Ness | 604/368 |
| 4,880,419 | 11/1989 | Ness | 604/368 |
| 4,904,249 | 2/1990 | Miller et al. | 604/378 |
| 4,960,477 | 10/1990 | Mesek | 156/209 |
| 4,973,325 | 11/1990 | Sherrod et al. | 604/368 |
| 4,994,037 | 2/1991 | Bernardin | 604/368 |
| 5,009,650 | 4/1991 | Bernardin | 604/378 |
| 5,034,007 | 7/1991 | Igaue et al. | 604/365 |
| 5,080,741 | 1/1992 | Nomura et al. | 156/201 |
| 5,098,423 | 3/1992 | Pieniak et al. | 604/385.1 |
| 5,110,386 | 5/1992 | Ochi et al. | 156/204 |
| 5,147,345 | 9/1992 | Young et al. | 604/378 |
| 5,464,402 | 11/1995 | Zajaczkowski | 604/385.1 |

SHAPED ABSORBENT CORES COMPRISING MULTIPLE PIECES OF ABSORBENT MATERIAL AND METHOD FOR MAKING SAME

FIELD OF THE INVENTION

This invention relates to shaped absorbent cores that are useful in absorbent articles, such as disposable diapers. This application further relates to a method for making such shaped absorbent cores from multiple pieces of absorbent members.

BACKGROUND OF THE INVENTION

Absorbent articles such as disposable diapers, incontinence pads, training pants, and catamenial napkins generally include an absorbent core for receiving and holding body exudates. The absorbent core typically includes a fibrous web, which can be a nonwoven, airlaid web of natural or synthetic fibers, or combinations thereof. Fibrous webs used in such absorbent articles also often include certain absorbent gelling materials usually referred to as "hydrogels," "superabsorbent" or "hydrocolloid" materials to store large quantities of the discharged body fluids. These materials absorb through capillary or osmotic forces, or a combination of both.

Alternative absorbent materials capable of providing capillary fluid transport are open-celled polymeric foams. If made appropriately open-celled polymeric foams provide features of capillary fluid acquisition, transport, and storage required for use in high performance absorbent cores for absorbent articles such as diapers. Absorbent articles containing such foams may also possess desirable wet integrity, provide suitable fit throughout the entire period the article is worn, and may avoid changes in shape during use. In addition, absorbent articles containing such absorbent foam structures could be easier to manufacture on a commercial scale. For example, absorbent foam diaper cores could simply be stamped out of continuous foam sheets and could be designed to have considerably greater integrity and uniformity than air-laid fibrous absorbent cores containing particulate absorbent gelling materials.

Besides absorbency and manufacturing ease, another desirable property of open-celled polymeric foams is the ability to make shaped or contoured absorbent cores having various shape configurations, fluid absorbency properties, and wear characteristics. For example, shaped or contoured absorbent cores made from open-celled foam materials having particularly desirable fluid transport characteristics are disclosed in U.S. Pat. No. 5,147,345 ('345 patent) issued to Young et al. on issued Sep. 15, 1992 and hereby incorporated herein by reference. The Young et al. '345 absorbent core comprises a fluid acquisition/distribution component that can be fibrous or foam based, as well as a fluid storage/redistribution component that comprises a hydrophilic, flexible, open-celled polymeric foam.

Forming shaped or contoured absorbent cores from foam materials, including those disclosed in Young et al. '345, is advantageous because the material is easily formed into webs that can be processed as rollstock. For example, the hourglass-shaped foam layer shown in FIGS. 2 and 9 of Young et al. '345 is typically made from web material that may be processed off of rollstock by notching, cutting, severing and otherwise shaping to form the hourglass-shaped piece. However, because each hourglass-shaped layer is cut from a single piece of material, it has substantially uniform material properties, and the absorptive characteristics of the layer are also substantially uniform. Therefore, fluid is absorbed from one layer to the next, from an acquisition layer to a storage layer, for example, if the absorbing layer capillary absorption pressure exceeds the desorption pressure of the donating layer. However, the use of an hourglass-shaped layer limits the overall efficiency of the absorbent core by placing material in areas where it may not be needed. For example, the acquisition layer may include material in the waist area where it is not typically needed, and the storage layer would include material in the crotch area where may not be desired. Also, in forming the hour-glass shapes, a significant amount of unusable foam scrap may be created.

Other absorbent materials, such as non-woven materials suitable for processing from rollstock, are also typically substantially uniform in nature. Therefore, although most materials easily processable from roll stock may be formed into shaped absorbent cores, the resulting absorbent cores have uniform material characteristics such as thickness and chemistry, resulting in uniform absorbent characteristics.

Accordingly, it would be desirable to be able to independently vary the material characteristics of an absorbent core in predetermined regions of an absorbent article, thereby varying the absorptive characteristics of the predetermined regions, but still be able to efficiently make the core from webs suitable for processing from rollstock in a manner that minimizes material use and scrap generation.

It would also be desirable to make an absorbent article with areas of the absorbent article subject to rapid fluid acquisition, such as the crotch area, tailored to provide rapid acquisition and distribution to other regions of the absorbent article tailored for fluid storage and/or redistribution.

It would be further advantageous to be able to independently vary all the material characteristics of various parts of an absorbent core, such as thickness, shape, and chemistry, thereby minimizing scrap while also providing for tailored absorbent characteristics, resulting in optimum fluid management and greater comfort to the wearer.

SUMMARY OF THE INVENTION

The present invention relates to shaped absorbent cores suitable for absorbing and retaining aqueous body fluids. The absorbent cores comprise a front panel and a back panel. The front and back panels are made from fluid absorbent material, and each has an inner end, an outer end, and two sides. The inner and outer ends of each front and back panel have a length, with the inner end of each being shorter than the outer length of each. Preferably the sides of each of the front and back panels are joined to their respective inner ends by an edge defining generally arcuate notches. The front and back panels may comprise multiple layers of absorbent material.

The absorbent cores also comprise a center section made from fluid absorbent material having first and second ends. The first end of the center section is in fluid communication with the front panel by overlapping the front panel intermediate the front inner and outer ends, and the second end is in fluid communication with the back panel by overlapping the back panel intermediate the back inner and outer ends. In a preferred embodiment the center section comprises at least one generally rectilinear absorbent strip member.

The present invention also relates to a method for preparing a shaped absorbent core which, in one embodiment, comprises the steps of providing at least one continuous rectilinear web of first absorbent material having a longitudinal axis and a pair of lateral edges defining a first width.

This web of first absorbent material eventually forms the center section of the absorbent core. In a preferred embodiment, three continuous rectilinear webs of first absorbent material comprise discrete layers, with at least one layer exhibiting better fluid acquisition or acquisition/ distribution properties, and at least on layer exhibiting better storage/redistribution properties.

In one embodiment a continuous rectilinear web of second absorbent material having a longitudinal axis and a pair of lateral edges defining a second width wider than the first width of the first absorbent material is formed with opposing generally arcuate notched areas in the lateral edges at spaced intervals along the web of second absorbent material. The web of second absorbent material is severed transversely along a line intersecting the opposed generally arcuate notched areas at spaced intervals to form sections having opposed notched ends The sections are then positioned such that the notched ends are spaced apart and overlap the continuous rectilinear web of first absorbent material, forming layers of absorbent material. Next, the layers of absorbent material are severed transversely at a point intermediate the notched ends, thereby forming a shaped absorbent core having a front panel and a back panel of second absorbent material overlying a center section of first absorbent material, the front and back panels and center section forming generally an elongated hourglass shape.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

DETAILED DESCRIPTION OF THE INVENTION

As used herein, the term "absorbent core" refers to a material or combination of materials suitable for absorbing, distributing, and storing aqueous fluids such as urine and certain other body exudates. The term "absorbent article" refers to devices which absorb and contain body exudates by use of an absorbent core, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner.)

Figure 2:
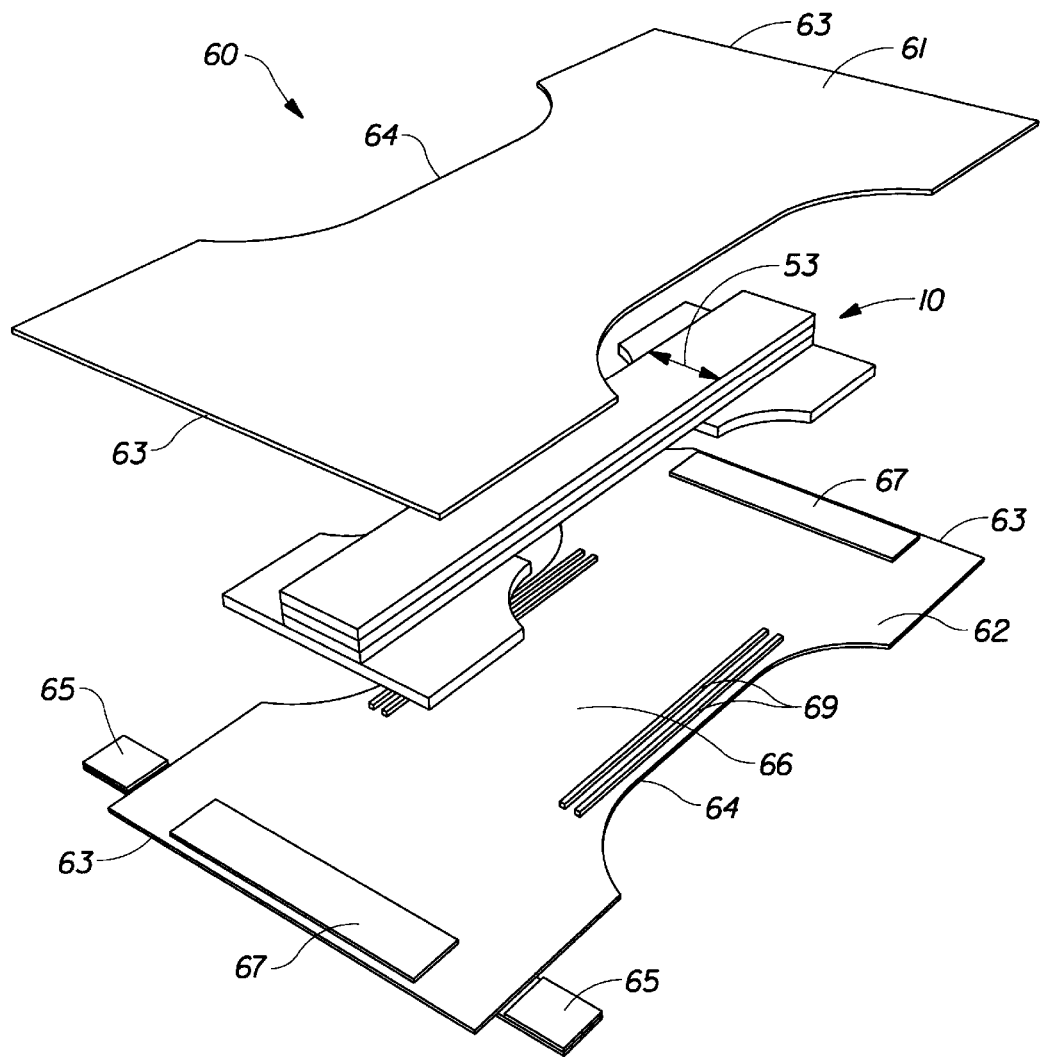
FIG. 2 is an exploded perspective view depicting a shaped absorbent core of the present invention in a disposable diaper.

A preferred embodiment of an absorbent article of the present invention is the disposable absorbent article, diaper 60, shown in FIG. 2. As used herein, the term "diaper" refers to an absorbent article generally worn by infants and incontinent persons that is worn about the lower torso of the wearer. It should be understood, however, that the present invention is also applicable to other absorbent articles such as incontinent briefs, incontinent undergarments, diaper holders and liners, training pants, pull-on diapers, feminine hygiene garments such as sanitary napkins, and the like.

The Shaped Absorbent Core

Figure 1:
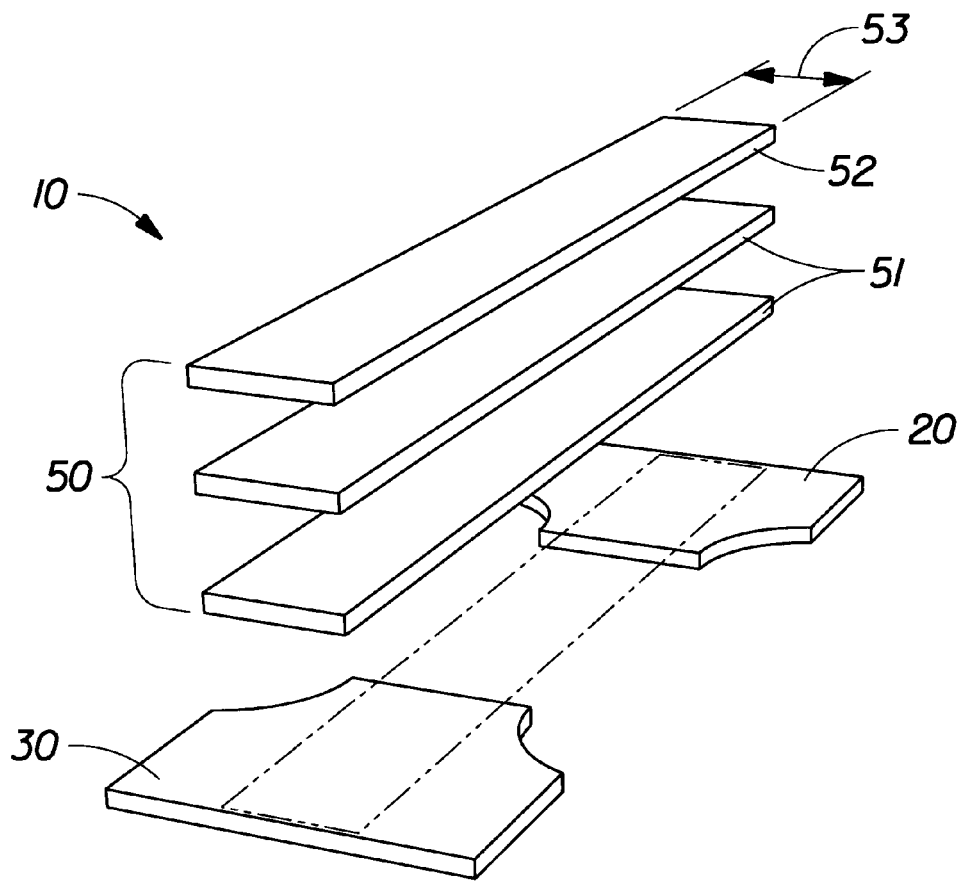
FIG. 1 is an exploded perspective view depicting the relationship between the elements of an embodiment of a shaped absorbent core of the present invention.
Figure 3:
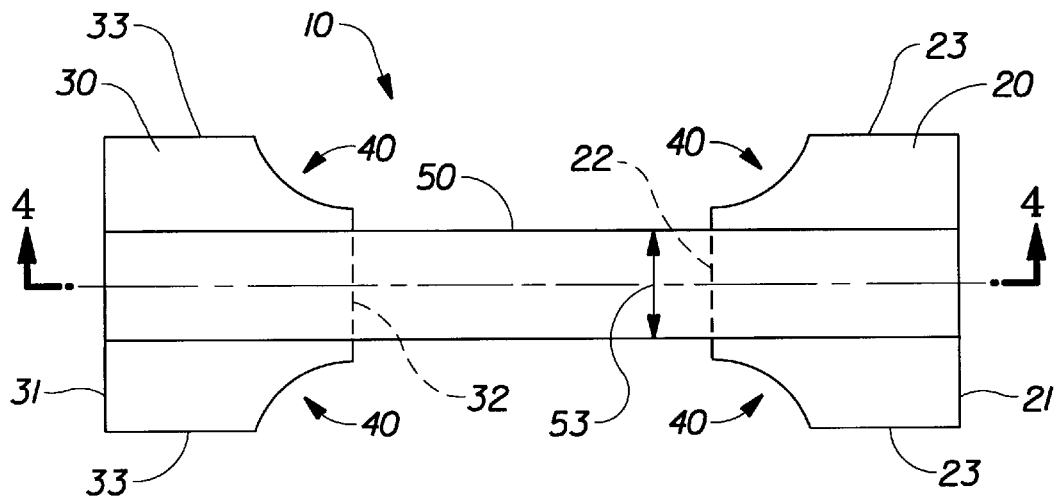
FIG. 3 shows a top plan view of a shaped absorbent core according to the present invention.

FIG. 1 shows an exploded perspective view depicting the elements of an embodiment of the shaped absorbent core 10 of the present invention such as may be used in an absorbent article, for example, in a disposable diaper. As depicted in FIGS. 1 and 3, the absorbent core 10 comprises a front panel 20 and a back panel 30, both made of absorbent material, preferably material suitable for fluid storage or storage/ redistribution. The front panel 20 has an outer front end 21, an inner front end 22, and a pair of sides 23. Similarly, the back panel 30 has an outer back end 31, an inner back end 32, and a pair of sides 33. The front panel 20 has cut-out areas 40 where material is removed at the intersection of the sides 23, and the inner front end 22. Similarly, the back panel 30 has cut-out areas 40 at the intersection of the sides 33, and the inner back end 32. The cut-out areas 40, or notched portions, join the sides and the inner ends such that the resulting widths of the inner ends 22 and 32 are narrower than that of the outer ends 21 and 31, respectively. By "notched" is meant that instead of a side and end meeting at a generally right angle, some amount of material is removed from the corner to produce an additional edge portion joining the side and end. The additional edge portion of notch 40 may be generally straight, but in a preferred embodiment it is concave and generally arcuate, as depicted in FIG. 3. It is also contemplated that the notch may have generally straight sides, with the limiting example resulting in a back or front panel being substantially trapezoidal-shaped.

In a generally flat, unfolded state, the front panel 20 and back panel 30 are positioned such that the inner front end 22 of front panel 20 is opposed to and spaced from the inner back end 32 of back panel 30 as shown in FIGS. 1–3. The distance between the front and back panels may be varied as necessary. In general the distance will increase as the crotch length increases with the size of the absorbent article.

FIG. 1 further shows the center section 50 of absorbent material overlying the front and back panels 20 and 30. Center section 50 is preferably generally rectilinear. By "generally rectilinear" is meant that preferably the center section is of substantially constant width along its length, so that it may be supplied off of roll stock when the absorbent core of the invention is made by the method of the present invention. In general, however, the center section 50 need only span and overlap front and back panels 20 and 30, and may have a varying width along its length. As shown, generally rectilinear center section 50 extends from about the outer front end 21 of front panel 20, to about the outer back end 31 of back panel 30. In use, it is only necessary that the center section is in fluid communication with front and back panels 20 and 30, with the ends of the center section overlapping front and back panels 20 and 30 intermediate their respective inner and outer ends.

For some materials and configurations it may be desirable to join the layers of the absorbent core by adhesive so as to fix predetermined regions in relative relation to adjacent layers. It is contemplated that fixably bonding the center section without overlapping the front or back panels may be desirable, as long as such bonding does not prevent fluid transfer. The method of joining, whether overlapped or not, may be by any suitable method known in the art, such as by spraying adhesive in target regions of the absorbent core during manufacture.

Center section 50 may comprise multiple strips of absorbent material, e.g., strips 51 and 52, each strip potentially having individual fluid acquisition, acquisition/distribution, storage, or storage/redistribution characteristics, as well as individual shape, width, length and thickness characteristics. For example, in a preferred embodiment, at least two relatively thin, flexible, resilient, polymeric foam strips 51 are made from the same storage/redistribution material as the front and back panels 20 and 30. The strips 51 and front and back panels 20 and 30, having similar absorptive characteristics and being in fluid communication, act as primary storage/redistribution members.

In a preferred embodiment generally rectilinear strip 52 comprises a relatively thin, flexible, resilient, polymeric foam material having greater fluid acquisition or acquisition/distribution characteristics than strips 51, thereby tending to quickly acquire and partition body exudates for more rapid absorption into storage/redistribution layers 51 and front and back panels 20 and 30.

The fluid absorbent members of the present invention can be utilized in disposable products which are capable of absorbing significant quantities of body fluids, such as urine, perspiration, menses, and water in body wastes. Such articles may be prepared in the form of disposable diapers, catamenial pads, adult incontinence briefs, and the like These absorbent articles generally comprise three basic structural components. As discussed in further detail below, with reference to FIG. 2, one such component is a substantially liquid impervious backsheet. On top of this backsheet is disposed an absorbent core which may itself comprise one or more distinct layers. On top of this absorbent core and joined to the backsheet is a fluid pervious topsheet. Preferably, the topsheet and backsheet are joined directly at the absorbent article's periphery by adhesive or other attachment means known in the art. The topsheet may also be adhered to the absorbent core.

FIG. 2 shows an exploded perspective view of an absorbent core 10 according to the present invention as contemplated for use in a disposable diaper 60. It should be understood, however, that the present invention is also applicable to other absorbent articles such as incontinent briefs, incontinent pads, training pants, diaper inserts, sanitary napkins, and the like. The diaper 60 depicted in FIG. 2 is a simplified absorbent article that could represent a diaper prior to its being placed on a wearer. It should be understood, however, that the present invention is not limited to the particular type or configuration of diaper shown in FIG. 2.

The disposable diaper 60 is shown in its uncontracted state (i.e., with generally all the elastic induced contraction removed) to more clearly show the construction of the diaper 60. The diaper 60 may comprise a liquid pervious topsheet 61; a liquid impervious backsheet 62 joined with the topsheet 61; and an absorbent core 10 is positioned between the topsheet 61 and the backsheet 62. Additional structural features such as elastic members and fastening means for securing the diaper in place upon a wearer (such as tape tab fasteners) may also be included.

While the topsheet 61, the backsheet 62, and the absorbent core 10 can be assembled in a variety of well known configurations, a preferred diaper configuration is described generally in U.S. Pat. No. 3,860,003 (Buell), issued Jan. 14, 1975, which is incorporated by reference. Alternatively preferred configurations for disposable diapers herein are also disclosed in U.S. Pat. No. 4,808,178 (Aziz et al.), issued Feb. 28, 1989; U.S. Pat. No. 4,695,278 (Lawson), issued Sep. 22, 1987; and U.S. Pat. No. 4,816,025 (Foreman), issued Mar. 28, 1989, all of which are incorporated by reference.

FIG. 2 shows a preferred embodiment of the diaper 60 in which the topsheet 61 and the backsheet 62 are co-extensive and have length and width dimensions generally larger than those of the absorbent core 10. The topsheet 61 is joined with and superimposed on the backsheet 62 thereby forming the periphery of the diaper 60. The periphery defines the outer perimeter or the edges of the diaper 60.

The topsheet 61 is compliant, soft feeling, and non-irritating to the wearer's skin. Further, the topsheet 61 is liquid pervious permitting liquids to readily penetrate through its thickness. A suitable topsheet 61 can be manufactured from a wide range of materials such as porous foams, reticulated foams, apertured plastic films, natural fibers (e.g., wood or cotton fibers), synthetic fibers (e.g., polyester or polypropylene fibers) or from a combination of natural and synthetic fibers. Preferably, the topsheet 61 is made of a hydrophobic material to isolate the wearer's skin from liquids in the absorbent core 10. A particularly preferred topsheet 61 comprises staple length polypropylene fibers having a denier of about 1.5, such as Hercules type 151 polypropylene marketed by Hercules, Inc. of Wilmington, Del. As used herein, the term "staple length fibers" refers to those fibers having a length of at least about 15.9 mm (0.62 inches).

There are a number of manufacturing techniques which can be used to manufacture the topsheet 61. For example, the topsheet 61 can be woven, nonwoven, spunbonded, carded, or the like. A preferred topsheet is carded, and thermally bonded by means well known to those skilled in the fabrics art. Preferably, the topsheet 61 has a weight from about 18 to about 25 grams per square meter, a minimum dry tensile strength of at least about 400 grams per centimeter in the machine direction, and a wet tensile strength of at least about 55 grams per centimeter in the cross-machine direction.

While it is preferred to have a topsheet as the material nearest the wearer's skin, it is not necessary. It is contemplated that a suitable absorbent core configuration could be used without a topsheet and still produce desirable results such as comfort and absorbency as well as simplicity in manufacturing and material cost savings. For example, the body-side surface of the absorbent core itself could be made of liquid pervious, soft, compliant, non-irritating materials that substitute for a separate topsheet. Such an absorbent core would only need to be used in combination with a backsheet to provide for comfort and absorbency in an absorbent article.

The backsheet 62 is impervious to liquids and is preferably manufactured from a thin plastic film, although other flexible liquid impervious materials may also be used. The backsheet 62 prevents the exudates absorbed and contained in the absorbent core 10 from wetting articles which contact the diaper 60 such as bed sheets and undergarments. Preferably, the backsheet 62 is polyethylene film having a thickness from about 0.012 mm (0.5 mil) to about 0.051 centimeters (2.0 mils), although other flexible, liquid impervious materials can be used. As used herein, the term "flexible" refers to materials which are compliant and which will readily conform to the general shape and contours of the wearer's body.

A suitable polyethylene film is manufactured by Monsanto Chemical Corporation and marketed in the trade as Film No. 8020. The backsheet 62 is preferably embossed and/or matte finished to provide a more clothlike appearance. Further, the backsheet 62 may be "breathable," permitting vapors to escape from the absorbent core 10 while still preventing exudates from passing through the backsheet 62. It is contemplated that a backsheet that is highly breathable but substantially impervious to liquid may be desirable for certain absorbent articles.

The size of the backsheet 62 is dictated by the size of the absorbent core 10 and the exact diaper design selected. In a preferred embodiment, the backsheet 62 has a modified hourglass-shape extending beyond the absorbent core 10 a minimum distance of at least about 1.3 centimeters to at least about 2.5 centimeters (about 0.5 to about 1.0 inch) around the entire diaper periphery.

The topsheet 61 and the backsheet 62 are joined together in any suitable manner. As used herein, the term "joined" encompasses configurations whereby the topsheet 61 is directly joined to the backsheet 62 by affixing the topsheet 61 directly to the backsheet 62, and configurations whereby the topsheet 61 is indirectly joined to the backsheet 62 by affixing the topsheet 61 to intermediate members which in turn are affixed to the backsheet 62. In a preferred embodiment, the topsheet 61 and the backsheet 62 are affixed directly to each other in the diaper periphery by attachment means (not shown) such as an adhesive or any other attachment means as known in the art. For example, a uniform continuous layer of adhesive, a patterned layer of adhesive, or an array of separate lines or spots of adhesive can be used to affix the topsheet 61 to the backsheet 62.

Tape tab fasteners 65 are typically applied to the waistband region 63 of the diaper 60 to provide a fastening means for holding the diaper on the wearer. The tape tab fasteners 65 depicted are representative only. The tape tab fasteners can be any of those well known in the art, such as the fastening tape disclosed in U.S. Pat. No. 3,848,594 (Buell), issued Nov. 19, 1974, which is incorporated by reference. These tape tab fasteners or other diaper fastening means are typically applied near the corners of the diaper 60.

Elastic members 69 are disposed adjacent the periphery of the diaper 60, preferably along each longitudinal edge 64, so that the elastic members tend to draw and hold the diaper 60 against the legs of the wearer. Additionally, elastic members 67 can be disposed adjacent either or both of the waistband regions 63 of the diaper 60 to provide a waistband as well as or rather than leg cuffs. For example, a suitable waistband is disclosed in U.S. Pat. No. 4,515,595 (Kievit et al.), issued May 7, 1985, which is incorporated by reference. In addition, a method and apparatus suitable for manufacturing a disposable diaper having elastically contractible elastic members is described in U.S. Pat. No. 4,081,301 (Buell), issued Mar. 28, 1978, which is incorporated by reference.

The elastic members are secured to the diaper 60 in an elastically contractible condition so that in a normally unrestrained configuration, the elastic members effectively contract or gather the diaper 60. The elastic members can be secured in an elastically contractible condition in at least two ways. For example, the elastic members can be stretched and secured while the diaper 60 is in an uncontracted condition. Alternatively, the diaper 60 can be contracted, for example, by pleating, and the elastic members secured and connected to the diaper 60 while the elastic members are in their unrelaxed or unstretched condition. The elastic members may extend along a portion of the length of the diaper 60. Alternatively, the elastic members can extend the entire length of the diaper 60, or any other length suitable to provide an elastically contractible line. The length of the elastic members is dictated by the diaper design.

In use, the diaper 60 is applied to a wearer by positioning one waistband region under the wearer's back, and drawing the remainder of the diaper 60 between the wearer's legs so that the other waistband region is positioned across the front of the wearer. The tape-tab 65 or other fasteners are then secured preferably to outwardly facing areas of the diaper 60. In use, disposable diapers or other absorbent articles incorporating the fluid absorbent members of the present invention tend to more quickly and efficiently distribute and store liquids and to remain dry due to the high absorbent capacity of the fluid absorbent members. Disposable diapers incorporating the fluid absorbent members of the present invention can also be thinner and more flexible.

When used as an absorbent core in a disposable diaper 60, a preferred embodiment of the core 10 according to the present invention is positioned such that acquisition/distribution strip 52 is in fluid communication with topsheet 61, and serves to quickly acquire and partition body exudates from the wearer's body to the generally more absorptive storage/redistribution strips 51 and front and back panels, 20 and 30. Adhesive bonding of acquisition/distribution strip 52 to topsheet 61 may enhance the fluid communication by providing interfacial bonding and preventing topsheet separation from impeding fluid flow.

Front panel 20 generally corresponds to the portion of the disposable diaper worn in the front of the wearer, with the outer front end 21 being generally near the wearer's waist area. Similarly, the back panel 30 corresponds to the portion of the disposable diaper worn in the back of the wearer, with the outer back end 31 being generally near the wearer's waist area. The generally rectilinear center section 50 has a width 53 corresponding to a suitable width for the crotch area 66 of a disposable diaper. As well, the length of center section 50 may be varied to provide a suitable fit for various wearer sizes.

FIG. 3 shows a top view of a shaped absorbent core 10 as contemplated in one embodiment of the present invention. As shown, the front and back panels 20 and 30, together with generally rectilinear center section 50, form generally an elongated hourglass shape suitable for use in a disposable diaper or similar absorbent article. In a preferred embodiment the width 53 of generally rectilinear center section 50 is suitable for comfortably fitting within the crotch area of the wearer when absorbent core 10 is incorporated into an absorbent article, such as a disposable diaper.

Figure 4:
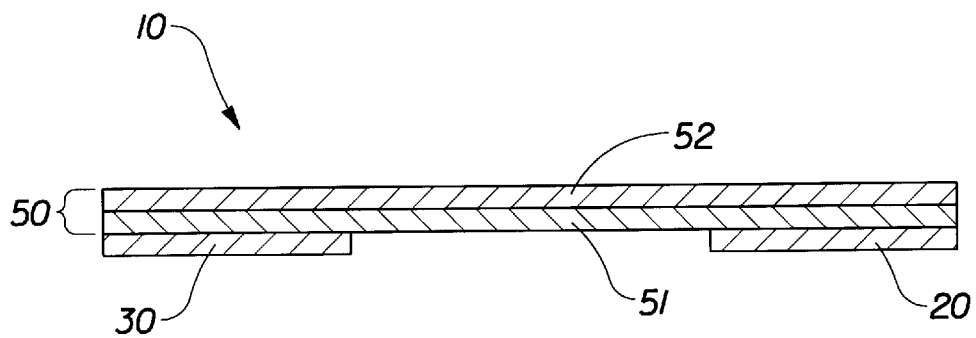
FIG. 4 shows a longitudinal cross-section of an embodiment of the shaped absorbent core depicted in FIG. 3.

The number and placement of strips 51 or 52 of the generally rectilinear center section 50 may be varied to achieve desired characteristics such as thinness, softness, flexibility, or beneficial fluid acquisition, distribution, and storage rates. For example, FIG. 4 shows in cross-section an embodiment of the present invention using one acquisition/distribution strip 52 and one storage/redistribution strip 51, both placed over front and back storage/redistribution panels 20 and 30, resulting in a thin, flexible absorbent core 10. By "over" is meant the side of the absorbent core of the invention corresponding to the wearer's body when used in an absorbent article such as a catamenial pad or disposable diaper. It is noted, however, that FIG. 4 is representative of one embodiment only, and it may be beneficial to place the strips 51 or 52 under the front and back panels 20 and 30. By "under" is meant the side of the absorbent core of the invention corresponding to the garment side when used in an absorbent article such as a catamenial pad or disposable diaper.

Figure 5:
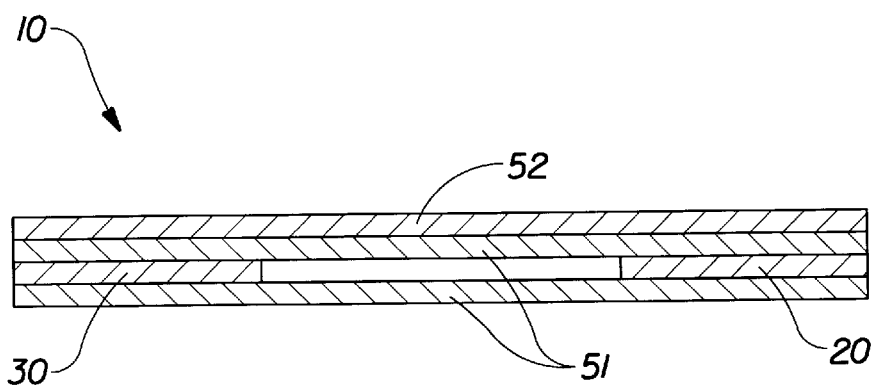
FIG. 5 shows in longitudinal cross-section another embodiment of a shaped absorbent core as depicted in FIG. 3.

FIG. 5 shows an alternative absorbent core 10 having two strips 51, one placed over front and back panels 20 and 30, and one placed under front and back panels 20 and 30. As shown in FIGS. 4 and 5, and as in the preferred embodiment of the present invention depicted in FIGS. 1 and 3, the acquisition strip 52 is generally on the side corresponding to the body side of an absorbent article, such as a disposable diaper. Therefore, acquisition/distribution strip 52 is generally in fluid communication with topsheet 61 of the disposable diaper, thereby acting to quickly acquire and partition body exudates to the lower storage/distribution layers 51 and storage/redistribution front and back panels 20 and 30.

Figure 6:
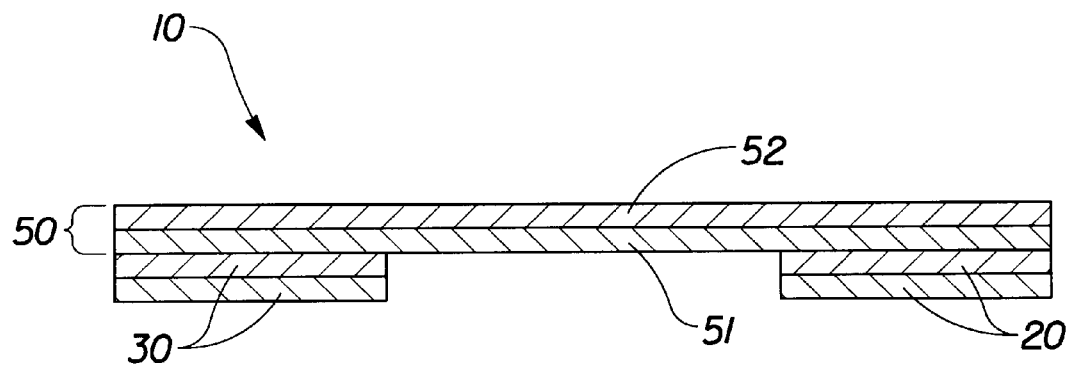
FIG. 6 shows in longitudinal cross-section an additional embodiment of a shaped absorbent core as depicted in FIG. 3.
Figure 7:
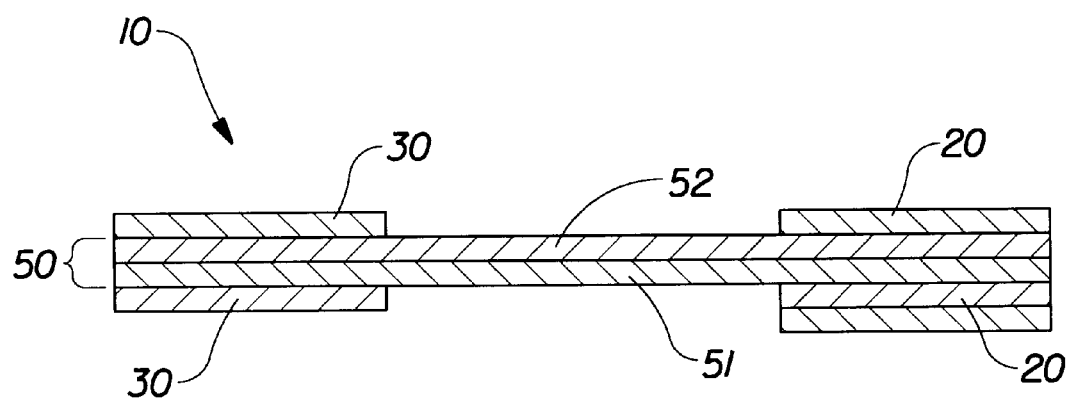
FIG. 7 shows in longitudinal cross-section still another embodiment of a shaped absorbent core similar to the core depicted in FIG. 3.

The number of layers of front and back panels 20 or 30 may also be varied to achieve desired characteristics such as beneficial fluid acquisition and distribution rates, as well as capacity and storage rates, as well as wearer comfort. For example, FIGS. 6 and 7 show in cross-section additional embodiments corresponding to the general top view of FIG. 3. FIG. 6 depicts two layers of front and back panels 20 and 30, both placed under generally rectilinear center section 50. FIG. 7 shows two layers of front and back panels 20 and 30, but in the embodiment depicted one layer is placed over generally rectilinear center section 5, and one layer is placed under, thereby "sandwiching" the ends of generally rectilinear center section 50.

By forming the absorbent core in sections, several desirable results are obtained. First, the core exhibits desirable aesthetics and fit when used in an absorbent article due to the use of discontinuous strips or panels of absorbent material. For example, when used in absorbent articles such as disposable diapers, the separate strips comprising the center section tend to bend and buckle somewhat independently from adjacent strips (and the from and rear panels) to provide better fit and comfort in the crotch area than is achieved with one-piece absorbent cores.

A second advantage to having the core formed in sections is the ability to independently tailor many of the characteristics of the absorbent members. These variations include the acquisition rates, distribution rates, storage capacities and rates, interfacial fluid transfer rates and efficiencies, thickness, functionality, and the shape or configuration of the absorbent strips or panels. For example, in a preferred embodiment of this invention, three absorbent strip members comprise the center section, with the absorbent strip member closest to the body of the wearer having relatively greater acquisition characteristics, and the remaining two having relatively greater acquisition/distribution characteristics. In this configuration bodily discharges, such as urine, are quickly acquired by the body-side acquisition layer and the desorbed into the adjacent acquisition/distribution layers for distribution to the front and back panels which preferably have greater storage/redistribution absorption characteristics.

It is contemplated that additional combinations of strip number, placement and absorptive characteristics may be used, with desired functional requirements influencing the ultimate design without departing from the scope of the present invention. For example, one beneficial configuration of generally rectilinear center section 50 is to have acquisition component strips on the body-side of the core as well as adjacent the backsheet. In this configuration fluid that seeps or drains to the backsheet can be quickly acquired and distributed to storage/redistribution components of the absorbent core, thereby minimizing opportunity for fluid leakage.

The Absorbent Materials

As described above, the absorbent core 10 comprises a plurality of discrete components, each component capable of having distinct fluid acquisition, acquisition/distribution, or storage/redistribution characteristics. In the context of the present invention, it should be noted that the term "fluid" means "liquid." So long as the acquisition, acquisition/distribution, and storage/redistribution components are in fluid communication with each other, they may be positioned relative to one another in a wide variety of configurations.

In general, any absorbent material having structural integrity such that it may be processed from roll stock by the method of the present invention may be utilized as the absorbent core 10 in an absorbent article of the present invention. Particularly preferred absorbent materials for use as absorbent components are foam-based in nature. Polymeric foams which are suitable for use in the fluid acquisition component can in general be characterized as structures which result when a relatively monomer-free gas or relatively monomer-free liquid is dispersed as bubbles in a polymerizable monomer-containing liquid, followed by polymerization of the polymerizable monomers in the monomer-containing liquid which surrounds the bubbles. The resulting polymerized dispersion can be in the form of a porous solidified structure which is an aggregate of cells, the boundaries or walls of which cells comprise solid polymerized material. The cells themselves contain the relatively monomer-free gas or relatively monomer-free liquid, which, prior to polymerization, had formed the "bubbles" in the liquid.

Particularly suitable absorbent foams for absorbent articles such as diapers have been made from High Internal Phase Emulsions (hereafter referred to as "HIPE"). See, for example, U.S. Pat. No. 5,260,345 issued to DesMarais et al. on Nov. 9, 1993, U.S. Pat. No. 5,268,224 issued to DesMarais et al. on Dec. 7, 1993, and U.S. Pat. No. 5,563,179 issued to Stone et al. on Oct. 18, 1996, each of which is hereby incorporated herein by reference. These absorbent HIPE foams provide desirable fluid handling properties, including: (a) relatively good acquisition rates to quickly acquire gushes of urine; (b) relatively good wicking and fluid distribution characteristics to transport the imbibed urine or other body fluid away from the initial impingement zone and into the unused balance of the foam structure to allow for subsequent gushes of fluid to be accommodated; and (c) a relatively high storage capacity with a relatively high fluid capacity under load, i.e. under compressive forces.

HIPE absorbent foams are also sufficiently flexible and soft so as to provide a high degree of comfort to the wearer of the absorbent article; some can be made relatively thin until subsequently wetted by the absorbed body fluid. See also the aforementioned Young et al. '345 patent, and U.S. Pat. No. 5,318,554 issued to Young et al. on Jun. 7, 1994, which discloses absorbent cores having a fluid acquisition/distribution component that can be a hydrophilic, flexible, open-celled foam such as a melamine-formaldehyde foam (e.g., BASOTECT® made by BASF), and a fluid storage/redistribution component that is a HIPE-based absorbent foam.

Representative materials suitable for use with the present invention are not limited to HIPE foams, and will now be described in greater detail.

The Acquisition Component

One element of the absorbent core is a fluid acquisition component which comprises a porous absorbent structure that has certain fluid handling characteristics with respect to discharged aqueous body fluids, e.g., urine, passing onto and into this structure through, for example, the topsheet of an absorbent article as described above. Since such fluid is frequently discharged in gushes, the acquisition component must be able to quickly acquire, temporarily hold, and also preferably transport (or partition) fluid, e.g., by wicking or other mechanisms, from the point of initial fluid contact to other parts of the acquisition component for eventual absorption into the adjacent fluid acquisition/distribution or storage/redistribution components.

Any porous absorbent material which will imbibe and partition aqueous body fluids to acquisition/distribution or storage/redistribution components of the core may be used as the acquisition layer 52. One measure of the fluid acquisition effectiveness of the absorbent material used to form the acquisition component is the Fluid Acquisition Rate, whereby measurements are made of the time taken for aliquots of synthetic urine test liquid deposited onto the surface of an absorbent material to be absorbed into the internal structure of the absorbent material. Suitable fluid acquisition rates and test methods are disclosed generally in the aforementioned Young et al. '345 patent. Accordingly, the fluid acquisition component should be fashioned from an absorbent material which exhibits an initial Fluid Acquisition Rate of at least about 2 ml of synthetic urine per second. More preferably, the fluid acquisition component will comprise an absorbent material which exhibits an initial Fluid Acquisition Rate of at least about 6 ml of synthetic urine per second. The "initial" fluid Acquisition Rate is the time taken for the first aliquot of such test liquid to be absorbed into the absorbent material before such material already contains any of the synthetic urine test liquid.

Preferred absorbent materials for the acquisition component include synthetic fiber nonwoven materials, cellulosic nonwoven materials, and various synthetic/cellulosic nonwoven materials. A preferred synthetic nonwoven material is disclosed in commonly assigned, U.S. Pat. No. 4,988,345 to Reising, issued Jan. 29, 1991, and U.S. Pat. No. 4,988,344 to Reising, issued Jan. 29, 1991, both of which are hereby incorporated herein by reference. The Reising acquisition layer comprises a first layer of hydrophilic fibrous material of lower average density than the other portions of the first layer so that it quickly acquires discharged liquids.

A preferred cellulosic nonwoven suitable for acquisition core components is formed from cellulose fibers that impart certain web and dry density characteristics to the absorbent core component. More specifically, the portions or regions of an absorbent core that acquire discharged bodily fluids will preferably have an average dry density of less than about 0.30 g/cc, and average density upon wetting with 1.0%, NaCl aqueous solution of less than about 0.20 g/cc, and an average dry basis weight from about 0.001 to about 0.10 $g/cm^2$. Preferred cellulosic nonwoven materials also comprise from about 50% to 100% chemically stiffened, twisted, and curled cellulosic fibers and from 0% to about 50% binding means. Such a cellulosic nonwoven is disclosed in the aforementioned Young '345 patent, and commonly assigned U.S. Pat. No. 5,531,728 to Lash, issued Jul. 2, 1996, which is hereby incorporated herein by reference.

The acquisition layer may be comprised of several different materials including nonwoven webs of synthetic fibers including polyester, polypropylene, or polyethylene, natural fibers including cotton or cellulose, blends of such fibers, or any equivalent materials or combinations of materials. Examples of such acquisition materials are more fully described in U.S. Pat. No. 4,950,264, to Osborn, issued on Aug. 21, 1990, which is hereby incorporated herein by reference.

Preferable thermoplastic binder means, including preferable thermoplastic fibers, are disclosed in commonly assigned U.S. Pat. No. 5,549,589 to Horney et al., issued on Aug. 27, 1996, which is hereby incorporated herein by reference. Thermoplastic binding means may include any hot melt adhesive which can be melted at temperatures which will not extensively damage the cellulosic fibers. Once thermally set, the resulting nonwoven material exhibits wet/dry mechanical properties such as flexibility, resiliency and structural integrity such that it may be processed as rollstock in the method of the present invention.

If chemical binding means are used to give the nonwoven structural integrity, preferably the absorbent member will comprise between about 80% and about 95% of the chemically stiffened fibers, from about 3% to 20% of a high surface area fiber, and from 0% to about 5% of a chemical additive binding means. A presently preferred chemical additive binding means is the commercially available polyacrylamide-glyoxal resin marketed by Cytec Industries, West Patterson, N.J., under the trade name Parez™ 631 NC. Additional suitable fiber types and chemical additive binder means are disclosed in commonly assigned Ser. No. 08/633, 630 to Seger et al., filed Apr. 17, 1996, the disclosure of which is hereby incorporated by reference.

Other acquisition materials may be prepared by wetlaying in accordance with commonly assigned U.S. Pat. No. 5,217, 445 to Young et al., issued Jun. 8, 1993, which is hereby incorporated herein by reference. In general, wetlaid webs can be made by depositing an aqueous slurry of fibers on to a foraminous forming wire, dewatering the wetlaid slurry to form a wet web, and drying the wet web. Further disclosure of particular wetlaying techniques suitable for forming an acquisition core component suitable for use in the present invention are disclosed in the aforementioned Young '345 patent. Besides acquiring body fluids rapidly, the absorbent acquisition component of the present invention should give up this fluid efficiently to other fluid acquisition/distribution or storage/redistribution components, including foam-based fluid storage components. Absorbent foams suitable for use as the acquisition component of the present invention combine relatively high capillary absorption pressures and capacity-per-weight properties (compared to conventional foams). Such foams are disclosed in U.S. Pat. No. 5,550,167 issued to Des Marais et al. on Aug. 27, 1996, which is hereby incorporated herein by reference.

The Fluid Acquisition/Distribution Components

The fluid acquisition/distribution components of the present invention may comprise similar materials as the acquisition component, with more distributive characteristics. Since discharged aqueous body fluid, e.g., urine, frequently discharge in gushes, the acquisition/distribution component must be able to quickly acquire and must also preferably transport fluid, e.g., by wicking or other mechanisms, from the point of initial fluid contact to other parts of the acquisition /distribution component for eventual absorption into the adjacent fluid storage/redistribution component. Such materials are preferably polymeric foam materials having a greater degree of distributive capacity such that body exudates may more efficiently be transported from the acquisition zone to the storage components of the absorbent core.

Absorbent materials comprising the fluid acquisition/distribution component of the articles herein will preferably be suitably effective at transporting absorbed liquid from one part or region of the acquisition/distribution component to another. Such liquid transport will frequently arise by virtue of the propensity of the acquisition/distribution component absorbent material to wick liquid through its structure. Accordingly, one measure of the fluid distribution effectiveness of the absorbent material used to form the acquisition/distribution component relates to the ability of such absorbent material to vertically wick synthetic urine.

Vertical wicking effectiveness can be measured and quantified in a number of ways, but one typical indicator of vertical wicking performance is the height to which a vertically positioned test strip of absorbent material will wick synthetic urine from a reservoir within a specified period of time. For purposes of the present invention, this height, termed the Vertical Wicking Height, is determined by the procedure described in the aforementioned Young et al. '345 patent. The fluid acquisition/distribution component of the articles herein will preferably be formed from absorbent material which exhibits a 30-minute Vertical Wicking Height of at least about 5 cm. More preferably, the fluid acquisition/distribution component will comprise absorbent material which has a 30-minute Vertical Wicking Height of at least about 10 cm, and most preferably the absorbent material which exhibits a Vertical Wicking Height of 25 cm.

Any porous absorbent material which will imbibe and partition aqueous body fluids to the extent set forth hereinbefore in terms of Fluid Acquisition Rate and preferably Vertical Wicking Height may be utilized as, or as part of, the fluid acquisition/distribution component of the absorbent articles herein. Frequently such absorbent material can be foam-based and/or fiber-based in nature.

A preferred embodiment utilizes an open-celled absorbent polymeric foam material that, in addition to functioning as an acquisition/distribution component in an absorbent core, has improved desorption properties to allow other core components having higher absorption pressures than the desorption pressure of the acquisition/distribution foam to partition away fluid. In particular, absorbent foams useful in or as the fluid acquisition/distribution component are those which have a pore volume of from about 2 to 100 ml/g, a capillary suction specific surface area of from about 0.2 to 1 $m^2$/g; a cell size of from about 10 to 300 microns and a density of from about 0.01 to 0.5 g/$cm^3$, provided valued for these parameters are selected so that the absorbent foams exceed the aforementioned Vertical Wicking Rate minimum.

The concepts of foam flexibility, hydrophilicity, pore volume, capillary suction, specific surface area, cell size, and density as relate to the present invention are described in greater detail in the aforementioned Young et al. '345 patent. Open-celled absorbent polymeric foam materials suitable for use as acquisition/distribution components in the present invention are described in the aforementioned Stone et al. '179 patent.

Other types of non-woven structures suitable for use as the fluid acquisition/distribution component include structures such as surfactant-treated bonded carded webs, webs of melt blown synthetic macrofibers or microfibers, pulp coformed webs, staple fiber coformed webs and the like. If non-woven fibrous absorbent structures are utilized in the present invention, such webs are preferably constructed essentially from hydrophilic chemically stiffened cellulosic fibers. Such cellulosic fibers are typically wood pulp fibers which have been stiffened with an intrafiber chemical stiffening agent and otherwise processed so they are formed into a twisted, curled configuration, as fully taught in the aforementioned Lash and Young et al. '345 patents, as well as the Seger '630 patent application.

Cellulosic fibers, in addition to being chemically stiffened, may also be advantageously combined with high surface area fibers, such as eucalyptus fibers, as disclosed in commonly assigned, co-pending Ser. No. 08/686,076, to Seger et al., filed Jul. 24, 1996, the disclosure of which is hereby incorporated herein by reference. The chemically stiffened fibers and eucalyptus fibers may be coformed in a stratified manner with thermoplastic binding means or chemical binding means, as taught in the aforementioned Seger '076 patent application.

The Fluid Storage/Redistribution Components

The absorbent core of the present invention comprises at least one, and preferable two, distinct fluid storage/redistribution components. The fluid storage/redistribution components act to store body exudates away from the wearers body so as to leave the wearer with a feeling of dryness and to prevent leakage. The storage/redistribution components are maintained in fluid communication with the acquisition or acquisition/distribution layer(s) such that urine or other aqueous body fluids present in the acquisition/distribution component can be desorbed, being absorbed by the fluid storage/redistribution component(s). Nonwovens as described above, particularly when combined with particulates of substantially water insoluble, absorbent hydrogel-forming polymer materials, may be useful as the fluid storage/redistribution component(s).

A preferred fluid storage/redistribution component of the absorbent core comprises cohesive sheets made from particulates of substantially water insoluble, absorbent hydrogel-forming polymer materials. Sheets may be made by layering predetermined amounts of the hydrogel-forming materials with cross-linking agents and curing. A preferred material of this type is disclosed in commonly assigned U.S. Pat. No. 5,324,561 to Rezai et al., issued Jun. 28, 1994, which is hereby incorporated herein by reference.

The most preferred fluid storage/redistribution component materials of the present invention comprise collapsible polymeric foam materials that, upon contact with aqueous fluids (in particular aqueous body fluids such as urine), may expand and absorb these fluids. These absorbent polymeric foam materials comprise a hydrophilic, flexible, nonionic polymeric foam structure of interconnected open-cells as disclosed in U.S. Pat. No. 5,387,207 issued to Dyer et al. on issued Feb. 7, 1995, and copending Ser. No. 08/563,866, entitled Absorbent Foam Materials for Aqueous Fluids Made From High Internal Phase Emulsions Having Very High Water-to-Oil Ratios, by DesMarais et al., filed Nov. 29, 1995, both of which are hereby incorporated by reference. Other suitable polymeric absorbent foam materials, material characteristics, and characterizing tests are disclosed and taught in the aforementioned Young et al. '345 patent.

The collapsible polymeric foam storage/redistribution component of the present invention may utilize low density (when expanded) absorbent foams. For a given expanded thickness, these lower density foams are thinner in their collapsed state than prior absorbent HIPE foams. These lower density foams more efficiently utilize the available polymer material and as a result provide an economically attractive means for achieving thinner absorbent cores for absorbent articles such as diapers, pull-up training pants, adult incontinence pads or briefs, sanitary napkins, and the like. This is achieved while retaining desired absorbency, dryness, and mechanical properties.

The Method and Apparatus for Making Shaped Absorbent Cores

Figure 8:
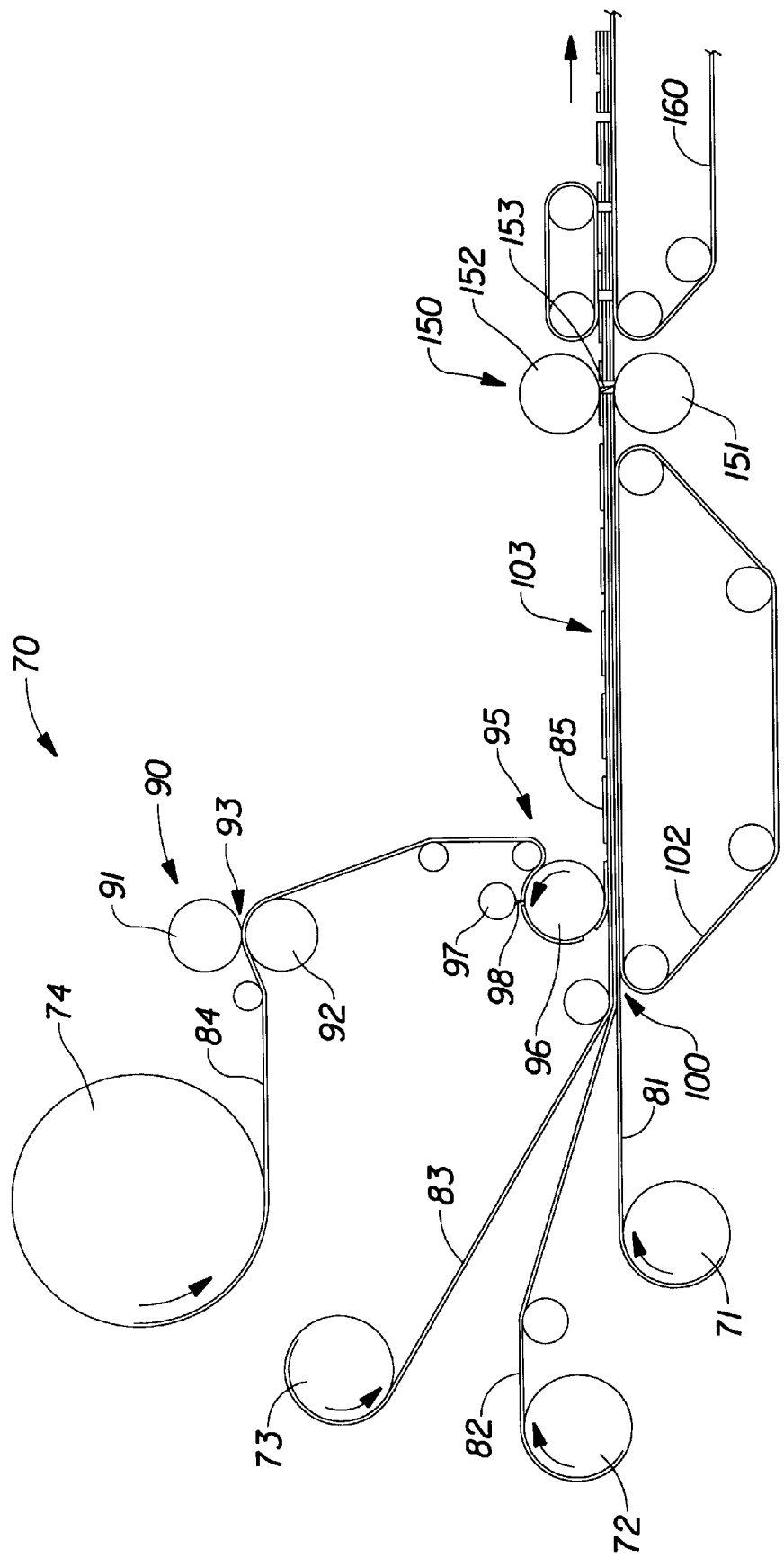
FIG. 8 schematically shows an apparatus for forming one embodiment of the shaped absorbent cores according to the method of the present invention.

A preferred method of making the shaped absorbent core of the present invention is now described with reference to FIGS. 8–15. FIG. 8 schematically shows a representative apparatus 70 suitable for accomplishing the method of forming the absorbent core components of the preferred embodiment of the present invention as depicted in FIG. 1. The method depicted in FIG. 8 and described in detail below can be easily modified to produce absorbent cores comprising different combinations and placement of absorbent members, such as those depicted in FIGS. 4–7. Representative modifications are shown schematically in FIGS. 9, 10 and 11 and, unless otherwise disclosed, can be understood with reference to the description of the method of FIG. 8 since like numerals identify like elements. The method of the present invention is not limited to nonwoven web materials or absorbent polymeric foam materials, but is suitable for use with any generally absorbent material formed into webs, either nonwoven or woven, fibrous or polymeric, as known in the art that may be supplied on rollstock and have sufficient integrity to be processed by the method of the present invention.

A first relatively narrow rectilinear web 81 is unwound from a supply roll 71. Web 81 has a width generally corresponding to width 53 of the generally rectilinear center section 50, as shown in FIGS. 1 and 2. Web 81 comprises a material suitable for use as an acquisition/distribution layer 52 of the preferred embodiment as shown in FIGS. 1 and 2. Web 81 is guided through entry point 100 onto a conveyor 102 where it is positioned for further processing as described below.

In a preferred embodiment, second and third relatively narrow rectilinear webs 82 and 83, comprised of a material suitable for acquisition/distribution or storage/redistribution of aqueous fluid, are unwound from supply rolls 72 and 73, respectively. Webs 82 and 83 correspond to storage/redistribution layers 51 of FIGS. 1 and 2 and may have a width generally corresponding to width 53 of the generally rectilinear center section 50, as shown in FIGS. 1 and 2. Webs 82 and 83 are guided through entry point 100 onto a conveyor 102 where they are positioned in layers upon web 81 for further processing as described below.

A relatively wide continuous rectilinear web 84 of absorbent material having a longitudinal axis and lateral sides is unwound from a supply roll 74. In a preferred embodiment, web 84 is suitable for use as a storage/redistribution member of the absorbent core 10, and is of a width suitable for forming into the front panel 20 and back panel 30 shown in FIGS. 1 and 3. The lateral sides of web 84 generally correspond to the sides 23 and 33 depicted in FIG. 3.

Figure 12:
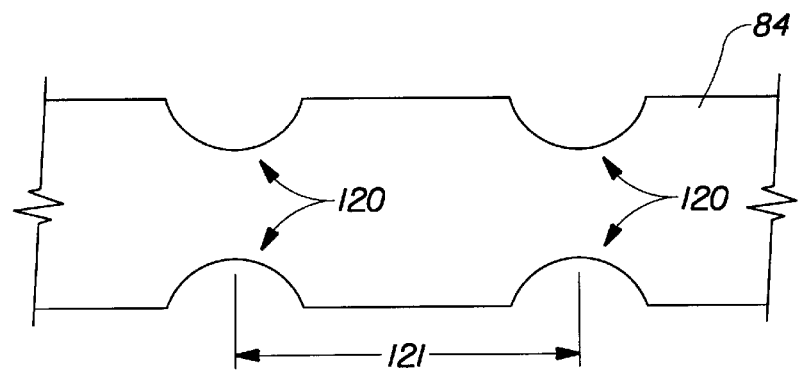
FIG. 12 is a plan view of a relatively wide continuous rectilinear web after notching.

Web 84 is guided from roll 74 to a notching apparatus 90. Notching apparatus 90 preferably comprises two nip rollers 91 and 92 through which web 84 is fed. As web 84 is fed through nip 93 of rollers 91 and 92, cutting blades (not shown) on roller 91 notch out substantially arcuate portions from opposing sides of web 84 so that as web 84 leaves the notching apparatus 90, it appears as shown in FIG. 12. FIG. 12 shows the continuous rectilinear web 84 with substantially arcuate notches 120 at spaced intervals 121 corresponding to the placement of the cutting blades on roller 91 shown in FIG. 6.

Figure 13:
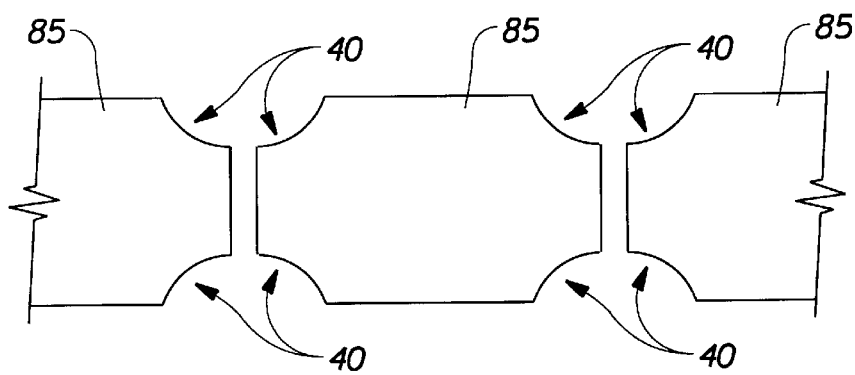
FIG. 13 is a plan view of a relatively wide continuous rectilinear web after a first cutting operation to produce discrete sections.

The continuous rectilinear web 84, notched as shown in FIG. 12, is next fed into a first slip, cut, and place assembly 95 for making cuts transverse to the longitudinal axis that sever the rectilinear web 84 into discrete sections 85, and to separate the discrete sections as shown in FIG. 13. Web 84 is guided onto rotating drum 96 that serves as a platen. Once in contact with the surface of rotating drum 96, and prior to being cut into discrete sections, web 84 is moving at a speed less than that of the surface of the drum and slips relative to the surface of the drum 96 under light vacuum applied through perforations in the surface of the drum along a portion of the drum's circumference. Cutting roller 97 rotates in concert with rotating drum 96, the diameter of cutting roller 97 being such that a cutting blade 98 attached to cutting roller 97 severs rectilinear web 84 at the spaced intervals 121 of FIG. 12, forming the discrete sections 85. Once web 84 is cut into discrete sections 85, a somewhat higher vacuum is applied along portions of the drum's circumference so that severed sections 85 remain in contact with the rotating drum 96, moving at the same speed as the surface of the drum in a spaced apart relationship. As shown in FIG. 13, the discrete sections 85 can best be described as generally rectangular in shape with notched corners 40, corresponding to the notches 40 of FIG. 1.

Figure 9:
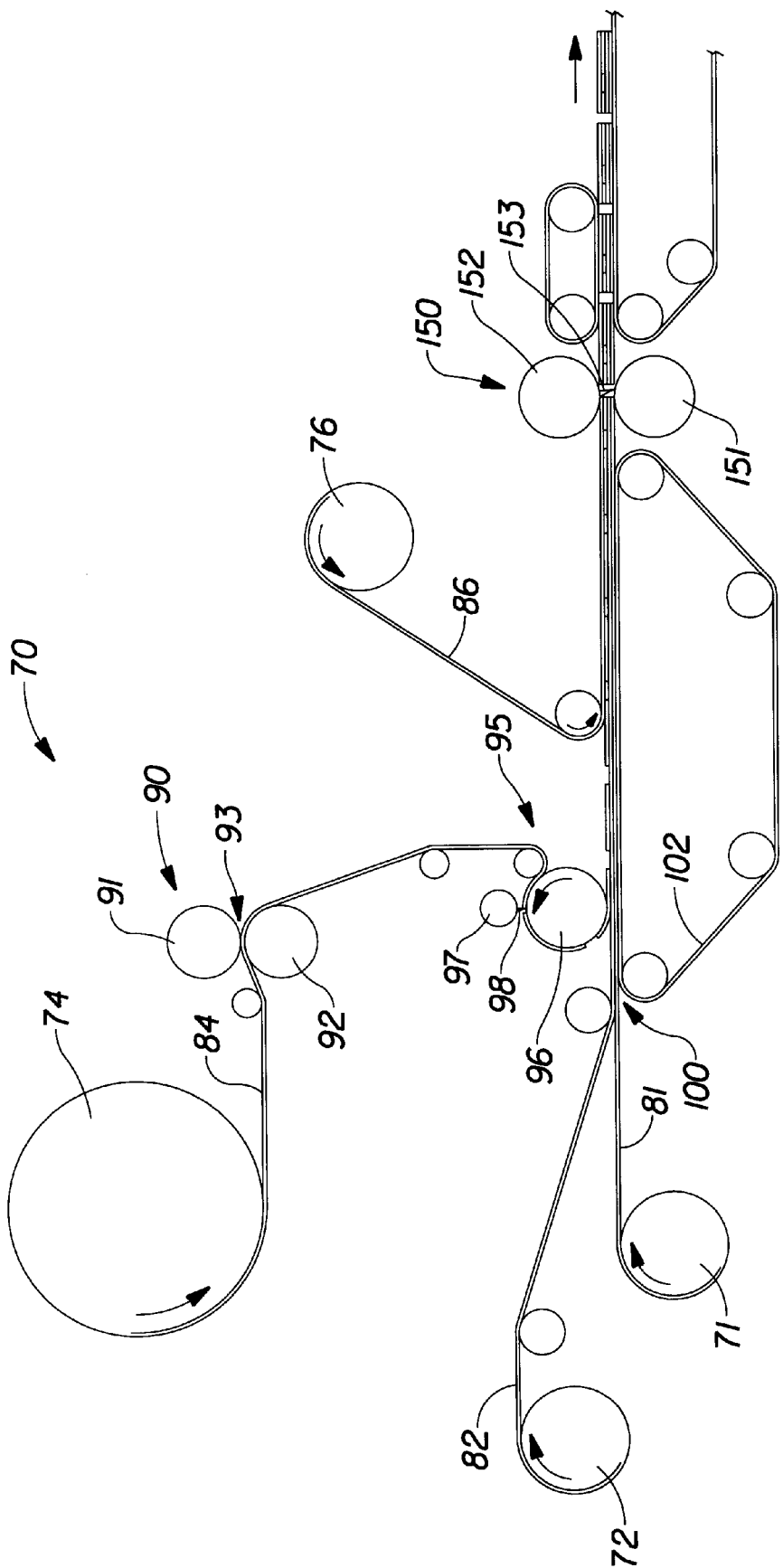
FIG. 9 schematically shows an apparatus for forming another embodiment of the shaped absorbent cores according to the method of the present invention.

The rotating drum 96 is positioned such that upon rotation, discrete sections 85 are released due to positive air pressure through perforations in the surface of the drum along a portion of the drum's circumference, and are urged into contact with layer 83 moving upon conveyor 102. The vacuum arrangement in rotating drum 96 is such that at the position of contact with layer 83, discrete section 85 is released from rotating drum 96 and continues to be carried upon layer 83 by conveyor 102. The linear velocity of conveyor 102 is generally equal to the tangential linear velocity of rotating drum 96, so discrete sections 85 are deposited in a spaced relationship onto layer 83, as depicted in FIG. 9.

Figure 14:
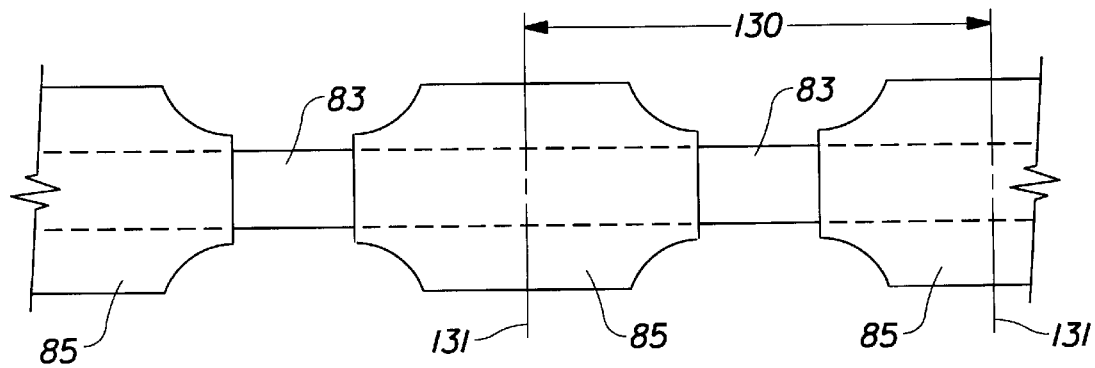
FIG. 14 is a plan view of the relatively wide rectilinear web discrete sections layered in spaced relationship on relatively narrow continuous rectilinear webs.

FIG. 14 shows in plan view the material being carried by conveyor 102 at, for example, point 103 in FIG. 8. Layer 83, and layers 82 and 81 below (not shown), form continuous rectilinear webs under discrete sections 85 laying in a spaced apart relationship. Discrete sections 85 are spaced apart at spaced intervals 130, corresponding generally with the distance between transverse centerlines 131 of adjacent discrete sections 85.

The material being carried on conveyor 102 is fed into knife assembly 150 for making transverse cuts severing all the layers of material. Cutting roller 152 has a diameter corresponding generally to the distance between the transverse centerlines 131 of discrete sections 85 as shown in FIG. 14. Roller 151 serves as a platen for a cutting blade 153 attached to cutting roller 152. Cutting blade 153 completely severs the layers at or near transverse centerlines 131 of discrete sections 85. Upon exiting knife 150, the absorbent material has been formed into the individual absorbent cores 10 of the present invention. Various known methods may be used to separate the individual absorbent cores 10, such as by varying the relative speeds of conveyors 102 and 160. The individual absorbent cores 10 are carried by conveyor 160 for further processing into absorbent articles, if necessary, and appear on conveyor 160 in plan view as shown in FIG. 15.

Figure 15:
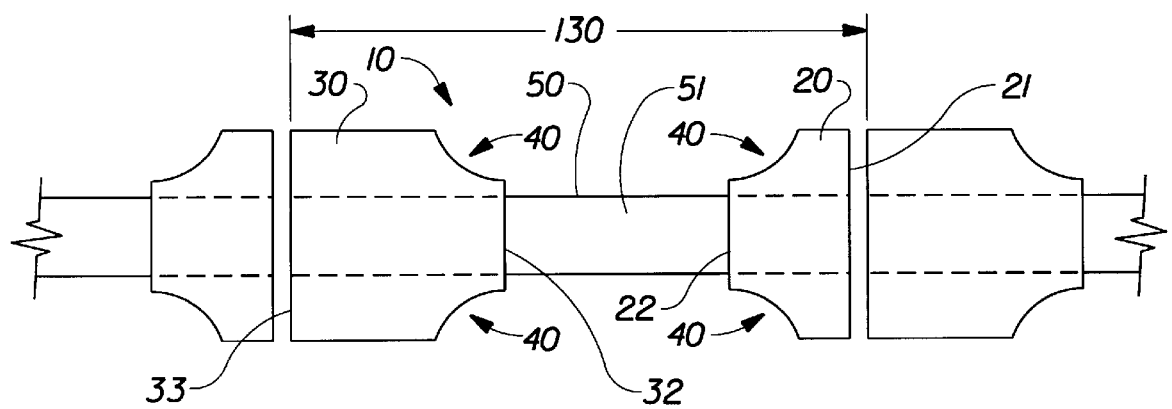
FIG. 15 is a plan view of finished shaped absorbent cores of the present invention as produced by a method of the present invention.

As shown in FIG. 15, it is not necessary for the length of front panel 20 measured from outer front end 21 to inner front end 22 to equal the length of the back panel 30 measured from its outer back end 31 to its inner back end 32. The position of the layered material on conveyor 102 in relation to knife assembly 150 determines the relative lengths of front panel 20 and back panel 30, and may be adjusted by the phase of knife assembly 150 in relation to conveyor 102. In a preferred embodiment of the present invention the back panel 30 is longer than the front panel 20 as depicted in FIG. 15. Such a configuration lends itself to a better fit when the absorbent core 10 is used in a disposable diaper.

As shown in FIGS. 13 and 14, the length of interval 130 may be varied to produce the desired length of generally rectilinear center section 50. It is desirable to be able to vary the length of center section 50 of an absorbent core 10 for use in disposable diapers to accommodate the difference in sizes of children or adults using such diapers.

FIG. 9 shows an embodiment of a method and apparatus of the invention as it may be to produce the core depicted in FIG. 5. Rather than a third relatively narrow rectilinear web 83, unwound from supply roll 73, relatively narrow rectilinear web 86 is unwound from supply roll 76. Web 86 is then guided to form a top layer of absorbent material on conveyor 102. The method continues as disclosed above to form the absorbent core depicted in FIG. 5.

Figure 10:
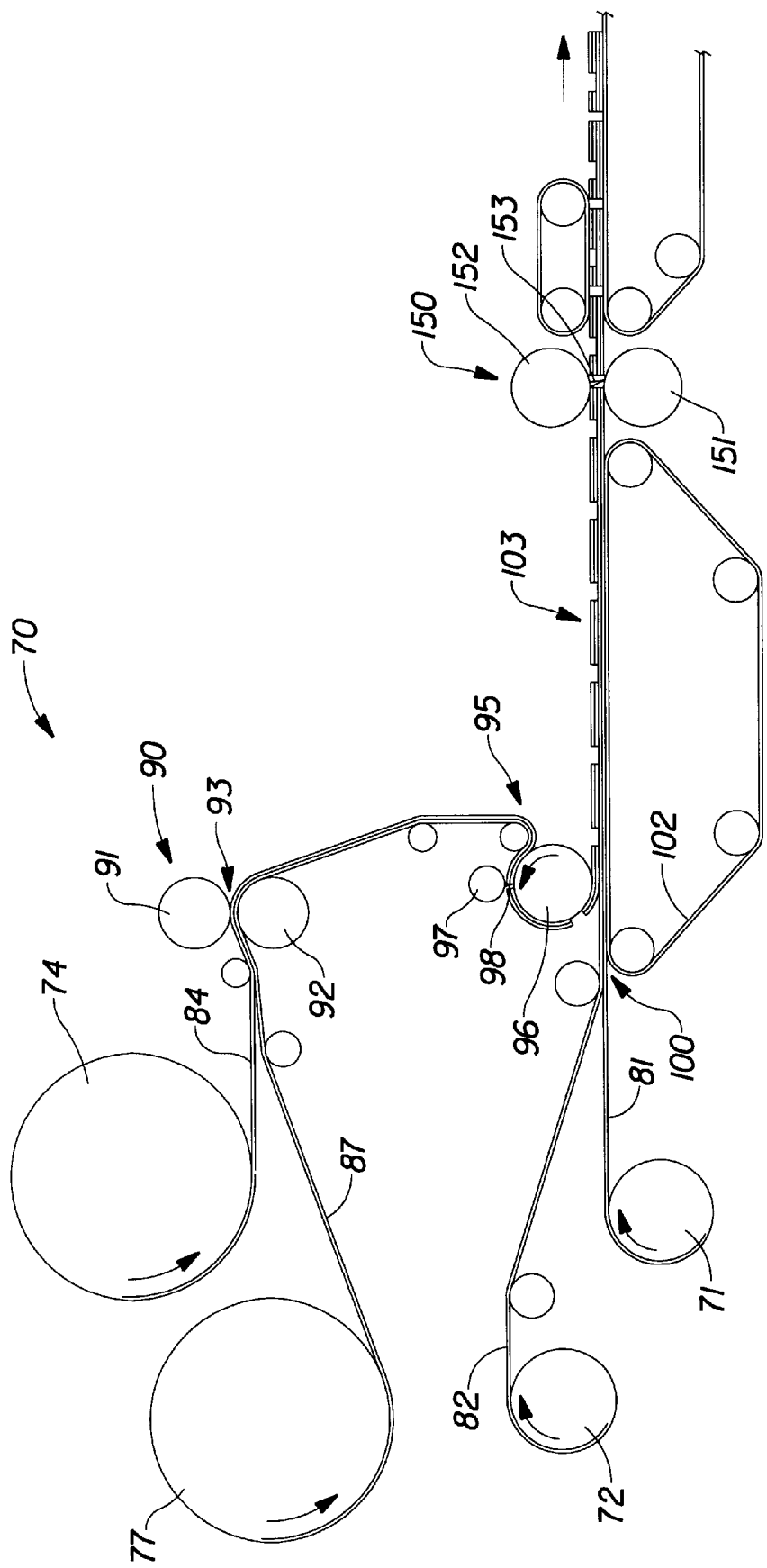
FIG. 10 schematically shows an apparatus for forming yet another embodiment of the shaped absorbent cores according to the method of the present invention.

FIG. 10 shows a representative method for forming the absorbent core 10 of the present invention as depicted in FIG. 6. In this embodiment, an additional relatively wide continuous rectilinear web 87 of absorbent material having a longitudinal axis and lateral sides is unwound from a supply roll 77 and is guided into contact and alignment with web 84 prior to entry into notcher 90. Webs 84 and 87 may be adhered together by known methods to facilitate proper alignment throughout the remainder of the process, particularly after being processed by slip and cut assembly 95.

Figure 11:
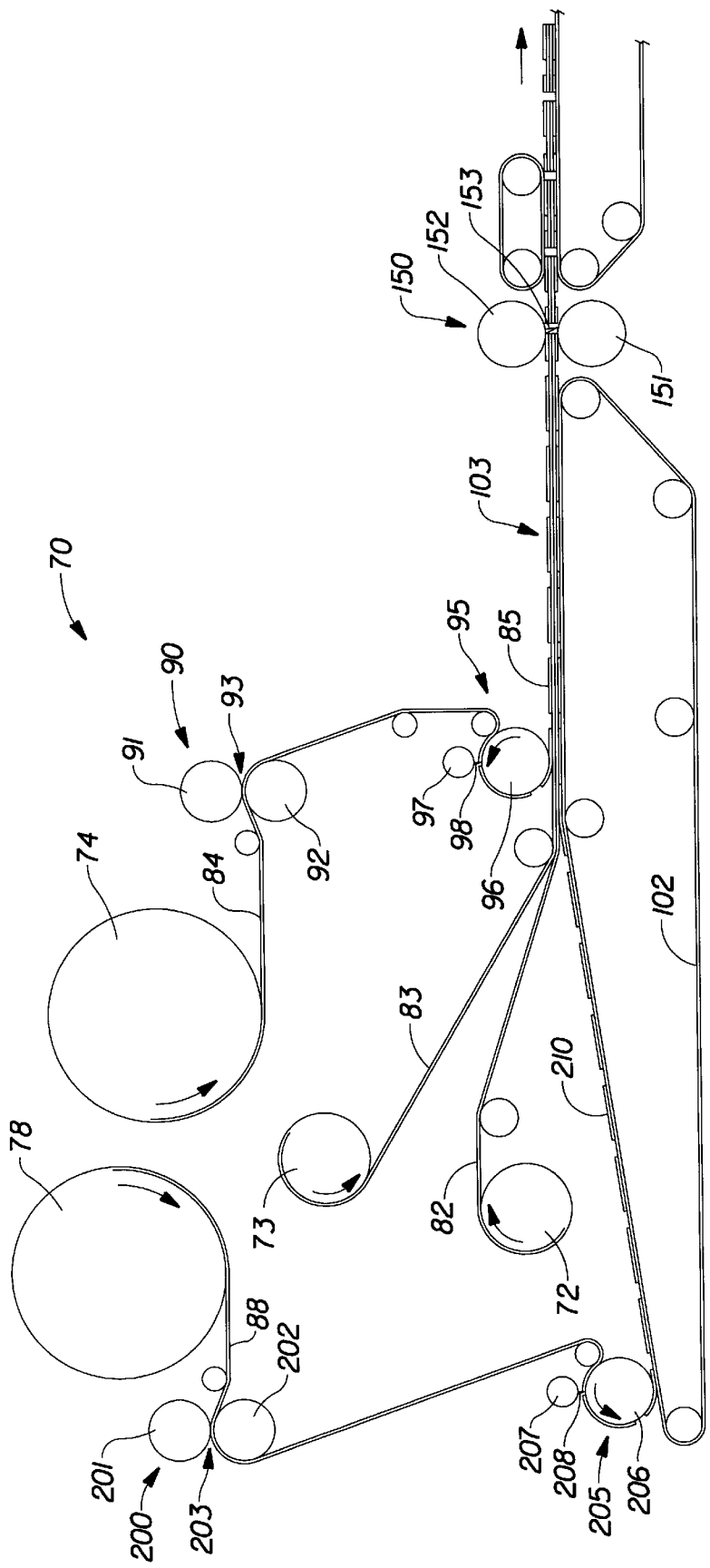
FIG. 11 schematically shows an apparatus for forming still another embodiment of the shaped absorbent cores according to the method of the present invention.

FIG. 11 depicts a representative method for forming the absorbent core 10 of the present invention as depicted in FIG. 7. In this embodiment of the method an additional relatively wide continuous rectilinear web 88 is unwound form a supply roll 78. Web 88 is guided from roll 78 to a notching apparatus 200 that operates in the same manner as notching apparatus 90 described above. Notching apparatus 200 preferably comprises two nip rollers 201 and 202 through which web 88 is fed. As web 88 is fed through nip 203 of rollers 201 and 202, cutting blades (not shown) on roller 201 notch out substantially arcuate portions from opposing sides of web 88 so that as web 88 leaves the notching apparatus 200, it appears generally similar to web 84 as shown in FIG. 12.

The continuous rectilinear web 88, notched generally as shown in FIG. 12, is next fed into a second slip, cut, and place assembly 205 for making cuts transverse to the longitudinal axis that sever and separate the rectilinear web 88 into discrete sections 210, generally similar in shape to discrete sections 85 as shown in FIG. 13. Web 88 is guided onto rotating drum 206 that serves as a platen. Once in contact with the surface of rotating drum 206, web 88 is moving at a speed less than that of the surface of the drum and slips relative to the surface of the drum 206 under light vacuum applied through perforations in the surface of the drum. Once web 88 is cut into discrete sections 210, a somewhat higher vacuum is applied so that severed sections 210 remain in contact with the rotating drum 206, moving at the same speed as the surface of the drum in a spaced apart relationship. Cutting roller 207 rotates in concert with rotating drum 206, the diameter of cutting roller 207 being such that a cutting blade 208 attached to cutting roller 207 severs rectilinear web 88 at spaced intervals analogous to the spaced intervals 121 of FIG. 12, forming the discrete sections 210. Discrete sections 210 can best be described as generally rectangular in shape with notched corners, corresponding to the notches 40 of FIG. 13.

The rotating drum 206 is positioned such that upon rotation, discrete sections 210 are brought into contact with conveyor 102. The vacuum arrangement in rotating drum 206 is such that at the position of contact with conveyor 102, discrete section 210 is released by positive air pressure from rotating drum 206 and continues to be carried upon conveyor 102. The linear velocity of conveyor 102 is generally equal to the tangential linear velocity of rotating drum 206, so discrete sections 85 are deposited in a spaced relationship onto conveyor 102, as depicted in FIG. 11. The remainder of the method of making proceeds as described above.

The method of the present invention provides a number of significant benefits. For example, the method generates significantly less scrap than would a typical method of forming a one-piece shaped absorbent core. Also, the method of the present invention provides for efficient supplying of webs of absorbent materials from is rollstock, especially foam, from which the panels and rectilinear strips are made. One advantage of such a process is a longer web roll life. For example, the narrower webs of absorbent material used to make the rectilinear strips can be spool wound for significantly longer roll life. A third benefit of the method of the present invention is greater control over certain processing variables, such as placement of core components in proper operating relationship. For example, because the wider web of absorbent material is notched and severed at the point the front and back panels are made, it is significantly easier to register the notched/severed panels in the appropriate relationship with the narrower rectilinear strip(s) to make the composite absorbent core.

While particular embodiments of the present invention have been illustrated and described, it would be obvious to those skilled in the art that various other changes and modification can be made without departing from the spirit and scope of the present invention. The foregoing is therefore intended to cover in the appended claims all such changes and modifications that are within the scope of the present invention.

What is claimed is:

1. A shaped absorbent core comprising:
    (a) a front panel comprising at least one layer of fluid absorbent material, said front panel having an inner front end and an outer front end, said outer front end having a length and said inner front end having a length less than said outer front end length;
    (b) a back panel comprising at least one layer of absorbent material, said back panel having an inner back end and an outer back end, said outer back end having a length and said inner back end having a length less than said outer back end length, said back panel being positioned so that said inner back end is opposed to and spaced apart from said inner front end of said front panel; and (c) a center section comprising at least one layer of fluid absorbent material having first and second ends, said first end being in fluid communication with said front panel by overlapping said front panel intermediate said front inner and outer ends, said second end being in fluid communication with said back panel by overlapping said back panel intermediate said back inner and outer ends.

2. The shaped absorbent core of claim 1, wherein said front panel further comprises first and second sides, each of said first and second sides joined to said front inner end by an edge defining a generally arcuate notch.

3. The shaped absorbent core of claim 1, wherein said back panel further comprises first and second sides, each of said first and second sides connected to said back inner end by edges defining a generally arcuate notch.

4. The shaped absorbent core of claim 1, wherein said fluid absorbent material comprises nonwoven fibrous material.

5. The shaped absorbent core of claim 1, wherein said fluid absorbent material comprises open-celled polymeric foam material.

6. The shaped absorbent core of claim 1, wherein said center section exhibits fluid acquisition properties in a fluid acquisition region and said front and back panels exhibit substantially fluid storage properties in fluid storage regions, such that fluid may be partitioned from fluid acquisition regions into fluid storage regions.

7. The shaped absorbent core of claim 1, wherein said center section comprises at least two generally rectilinear absorbent strip members.

8. The shaped absorbent core of claim 7, wherein at least one of said generally rectilinear absorbent strip members exhibits fluid acquisition properties.

9. The shaped absorbent core of claim 7, wherein at least one of said generally rectilinear absorbent strip members exhibits fluid distribution properties.

10. The shaped absorbent core of claim 7, wherein at least one of said generally rectilinear absorbent strip members exhibits fluid storage/redistribution properties.

11. The shaped absorbent core of claim 1, wherein said inner front end and said outer front end define a front panel length and said inner back end and said outer back end define a back panel length, such that said front panel length is substantially equal to said back panel length.

12. The shaped absorbent core of claim 1, wherein said inner front end and said outer front end define a front panel length and said inner back end and said outer back end define a back panel length, such that said front panel length is less than said back panel length.

13. The shaped absorbent core of claim 1, wherein said first end of said center section terminates substantially concurrently with said outer front end of said front panel, and said second end of said center section terminates substantially concurrently with said outer back end of said back panel.

14. An absorbent article capable of acquiring, distributing, and storing bodily fluids, said absorbent article comprising:
(a) a backsheet; and
(b) a shaped absorbent core disposed adjacent said backsheet, said absorbent core comprising:
a front panel comprising at least one layer of fluid absorbent material, said front panel having an inner front end and an outer front end, said outer front end having a length and said inner front end having a length less than said outer front end length;
a back panel comprising at least one layer of fluid absorbent material, said back panel having an inner back end and an outer back end, said outer back end having a length and said inner back end having a length less than said outer back end length, said back panel being positioned so that said inner back end is opposed to said inner front end of said front panel; and
a center section comprising at least one layer of fluid absorbent material having first and second ends, said first end being in fluid communication with said front panel by overlapping said front panel intermediate said front inner and outer ends, said second end being in fluid communication with said back panel by overlapping said back panel intermediate said back inner and outer ends.

15. The absorbent article of claim 14, wherein said absorbent article comprises a disposable diaper.

* * * * *

UNITED STATES PATENT AND TRADEMARK OFFICE
CERTIFICATE OF CORRECTION

PATENT NO.   : 5,906,602
DATED        : May 25, 1999
INVENTOR(S)  : Weber et al.

Page 1 of 1

It is certified that error appears in the above-identified patent and that said Letters Patent is hereby corrected as shown below:

Column 5,
Line 59, after "like" please insert therefor -- . -- (a period).

Column 6,
Line 20, after "10" please delete "is".

Column 9,
Line 49, after "section" please delete "5" and insert therefor -- 50 --.

Column 18,
Line 32, between "from" and "rollstock" please delete "is".
Line 58, after first occurrence of "front end" please insert therefor -- defining a front edge of a crotch portion --.
Line 58, after second occurrence of "front end" please insert therefor -- adjacent a waist edge --.
Line 62, after "back end" please insert therefor -- defining a back edge of said crotch portion --.
Line 63, after "back end" please insert therefor -- adjacent a waist edge --.

Column 20,
Line 30, after "opposed to" please insert therefor -- and spaced apart from --.

Signed and Sealed this

Seventeenth Day of December, 2002

JAMES E. ROGAN
*Director of the United States Patent and Trademark Office*